United States Patent [19]
Osborne et al.

[11] Patent Number: 5,633,008
[45] Date of Patent: May 27, 1997

[54] METHOD OF ADMINISTERING NICOTINE TRANSDERMALLY

[76] Inventors: James L. Osborne, 2365 Thompson Ct., Mountain View, Calif. 94043; Melinda K. Nelson, 1127 Hollenbeck, Sunnyvale, Calif. 94087; David J. Enscore, 18291 Montpere Way, Saratoga, Calif. 95070; Su I. Yum, 1021 Runnymead Ct., Los Altos, Calif. 94022; Robert M. Gale, 1276 Russell Ave., Los Altos, Calif. 94022; Donna D. Causey, 1286 Calle Aurora, Camarillo, Calif. 93010

[21] Appl. No.: 105,262

[22] Filed: Aug. 12, 1993

Related U.S. Application Data

[63] Continuation of Ser. No. 662,857, Mar. 1, 1991, which is a continuation of Ser. No. 537,672, filed as PCT/US89/02561, Jun. 13, 1989 published as WO89/12470, Dec. 28, 1989, Pat. No. 5,004,610, which is a continuation of Ser. No. 206,546, Jun. 14, 1988, abandoned.

[51] Int. Cl.⁶ .................................................. A61F 13/00
[52] U.S. Cl. ........................ 424/448; 424/449; 514/813
[58] Field of Search .............................. 424/449, 448; 514/813

[56] References Cited

U.S. PATENT DOCUMENTS

| | | | |
|---|---|---|---|
| 3,252,802 | 5/1966 | Cunningham | 99/2 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,845,217 | 10/1974 | Ferno et al. | 426/3 |
| 3,870,794 | 3/1975 | Hutchinson et al. | 424/264 |

(List continued on next page.)

FOREIGN PATENT DOCUMENTS

| | | | |
|---|---|---|---|
| 8145487 | 6/1988 | Australia | A61K 9/66 |
| 0117027 | 8/1984 | European Pat. Off. | A61M 37/00 |
| 0273004 | 11/1987 | European Pat. Off. | A61M 35/00 |
| 0251425 | 1/1988 | European Pat. Off. | A61K 9/00 |
| 0305757 | 8/1988 | European Pat. Off. | A61L 15/03 |
| 860152 | 3/1985 | Germany | A81K 4/85 |
| 3438284 | 3/1985 | Germany | A81K 31/485 |
| 61-251619 | 11/1986 | Japan | A61K 9/70 |
| 2171906 | 9/1986 | United Kingdom | A61K 9/00 |
| 8702870 | 5/1987 | WIPO . | |
| 8801516 | 3/1988 | WIPO . | |

OTHER PUBLICATIONS

S.H. Gelberg, W.A. Williams and J.I. Freeman, "Protective Clothing as a Means of Reducing Nicotine Absorption in Tobacco Harvesters," Archives of Environmental Health, pp. 111–114 Mar./Apr. 1979.

C. Carruthers, A. Neilson, "A Simplified Procedure for the Gas Chromatographic Determination of Nicotine: Application of the Method of Mouse Skin," Mikrochimica Acta [Wein] 1980 11, pp. 59–66.

(List continued on next page.)

*Primary Examiner*—D. Gabrielle Phelan

[57] ABSTRACT

A method of administering nicotine transdermally in which a nicotine patch, capable of administering nicotine for at least 16 hours at rates that are efficacious in smoking cessation therapy, is applied in the morning upon waking and removed prior to sleep. This method is effective even though nicotine is not essential during sleep and many smokers experience morning craving.

9 Claims, 1 Drawing Sheet

U.S. PATENT DOCUMENTS

| | | | |
|---|---|---|---|
| 3,877,468 | 4/1975 | Lichteneckert et al. | 131/2 |
| 3,901,248 | 8/1975 | Lichtneckert et al. | 131/2 |
| 3,926,188 | 12/1975 | Baker et al. | 424/427 |
| 3,996,245 | 12/1976 | Hartog et al. | 260/340.9 |
| 4,031,894 | 6/1977 | Urquhart et al. | 128/268 |
| 4,060,084 | 11/1977 | Chandrasekaran et al. | 128/260 |
| 4,125,623 | 11/1978 | Hartog et al. | 424/278 |
| 4,144,317 | 3/1979 | Higuchi et al. | 424/21 |
| 4,201,211 | 5/1980 | Chandrasekaran et al. | 128/268 |
| 4,379,454 | 4/1983 | Campbell et al. | 604/897 |
| 4,562,075 | 12/1985 | Rajadyaksha | 514/788 |
| 4,573,995 | 3/1986 | Cheng et al. | 604/896 |
| 4,588,580 | 5/1986 | Gale et al. | 424/21 |
| 4,597,961 | 7/1986 | Etscorn | 424/28 |
| 4,623,346 | 11/1986 | von Bittera et al. | 604/896 |
| 4,643,856 | 2/1987 | Nichols | 264/41 |
| 4,665,069 | 2/1987 | Rosenberg | 514/222 |
| 4,704,282 | 11/1987 | Campbell et al. | 424/449 |
| 4,715,387 | 5/1987 | Rose | 131/270 |
| 4,748,181 | 5/1988 | Hutchinson et al. | 514/343 |
| 4,758,434 | 7/1988 | Kydonieus et al. | 424/449 |
| 4,781,924 | 11/1988 | Lee et al. | 424/449 |
| 4,797,284 | 1/1989 | Lofer et al. | 424/449 |
| 4,837,027 | 5/1989 | Lee et al. | 424/449 |
| 4,839,174 | 6/1989 | Baker et al. | 424/270 |
| 4,915,950 | 4/1990 | Miranda et al. | 424/448 |
| 4,920,989 | 5/1990 | Rose et al. | 131/270 |
| 4,943,435 | 7/1990 | Baker et al. | 424/448 |
| 4,946,853 | 8/1990 | Bannon et al. | 514/343 |

OTHER PUBLICATIONS

H. Schievelbein, "Nicotine, Resorption and Fate," Pharmac. Ther., vol. 18, pp. 233–248, 1982.

J.E. Rose, M.E. Jarvik, K.D. Rose, "Transdermal Administration of Nicotine," Drug and Alcohol Dependence, 13 (1984), pp. 209–213.

J.E. Rose, J.E. Herskovic, Y. Trilling, M.E. Jarvik, "Transdermal Nicotine Reduces Cigarette Craving and Nicotine Preference," Clin. Pharmcol. Ther., pp. 450–456, Oct. 1985.

"Longterm Effects of Transdermal Nicotine Substitution in Behavioral Smoking Cessation," G. Buckremer, et al. Abstracts, 6th World Conference on Smoking and Health, Nov. 9–12, Tokyo, Japan.

Taylor, Stanley H., Scientific and Clinical Experience with Transdermal Nitroglycerin, American Hearth Journal 112(1), 197–207 (1986).

Flaherty, John T., Hemodynamic Attenuation and the Nitrate–Free Interval: Alternative Dosing Strategeis for Transdermal Nitroglycerin, The American Journal of Cardiology, p. 321, V. 56 (1985).

Jordan, Randy A. et al., Dose Requirements and Hemodynamic Effects of Transdermal Nitroglycerin Compared with Placebo in Patients with Congestive Heart Failure, Circulation, pp. 980–986, V. 71, No. 5, May 1985.

Baker, R.W., et al., "Controlled Release: Mechanisms and Rates," Advanced Experimental Med. Biol., vol. 47, pp. 15–71 (1974).

Baker, R. W., "Analysis of Transdermal Drug Delivery Patents, 1934–1984," Membrane Technology and Research, Inc., pp. 1–10.

Russell, "Nicotine Replacement: The Role of Blood Nicotine Levels, Their Rate of Change, and Nicotine Tolerance".

1

METHOD OF ADMINISTERING NICOTINE TRANSDERMALLY

CROSS-REFERENCE TO RELATED PATENT APPLICATIONS

This application is a continuation of coassigned application of Osborne et al., Ser. No. 07/662,857 filed Mar. 1, 1991, which is a continuation of coassigned application of Osborne, et al, Ser. No. 07/537,672 filed Jun. 14, 1990, for Subsaturated Nicotine Transdermal Therapeutic System now U.S. Pat. No. 5,004,610 which is a continuation-in-part of coassigned PCT/U.S. application Ser. No. 89/02561 of Osborne, et al, filed Jun. 13, 1989, for Subsaturated Transdermal Delivery Device which is a continuation of Ser. No. 07/206,546, filed Jun. 14, 1988, now abandoned. This application is related to the coassigned patent application of Enscore, et al, Ser. No. 07/284,283 filed Dec. 14, 1988, now abandoned, which is a continuation-in-part of the application of Enscore, et al, for a Subsaturated Transdermal Therapeutic System Having Improved Release Characteristics, U.S. Ser. No. 06/906,730 filed Sep. 12, 1986, and now U.S. Pat. No. 4,908,027 dated Mar. 13, 1990, which is incorporated herein by reference. It is also related to copending, coassigned application of Wang, et al, for Polyisobutylene Adhesive For Transdermal Devices, filed Apr. 16, 1990, Ser. No. 07/509,644 now U. S. Pat. No. 5,508,038, and coassigned application for the reissue of U.S. Pat. 4,781,924, Ser. No. 07/606,462 filed Oct. 31, 1990.

FIELD OF THE INVENTION

This invention relates to the transdermal administration of nicotine for an extended period of time for smoking cessation.

BACKGROUND OF THE INVENTION

Transdermal devices for the delivery of a wide variety of biologically active agents have been known for some time and representative systems which utilize rate controlling membranes and in-line adhesives are disclosed in U.S. Pat. Nos. 3,598,122; 3,598,123; 3,742,951; 4,031,894, 4,144, 317; 4,201,211 and 4,379,454 which are incorporated herein by reference. Such devices generally comprise an impermeable backing, a drug or active agent reservoir and a contact adhesive layer which can be laminated or heat sealed together to produce a transdermal delivery device and an agent release rate controlling membrane is often included between the reservoir and the skin.

It has also been proposed to deliver nicotine transdermally to aid in the cessation of smoking, see for example U.S. Pat. Nos. 4,597,961, 4,758,434, and 4,839,174 which are incorporated herein by reference.

Although the devices of the prior art have been found useful for the delivery of a wide variety of agents, we have encountered significant problems in producing devices intended to deliver nicotine, an oily, liquid material having a high solubility in medically acceptable contact adhesives.

As used herein, the expression "high nicotine solubility" as it relates to adhesives, is used to mean that nicotine is soluble in the adhesive to the extent that, at saturation, the adhesive layer is, (a) dissolved by nicotine; (b) becomes plasticized to the extent that it loses its cohesiveness or adhesiveness; or (c) contains concentrations of nicotine that produce adverse biological reactions when maintained in contact with the skin.

Regardless of the initial, as manufactured, concentration of active agent in the reservoir and other elements of typical prior art transdermal devices, such devices will equilibrate upon standing and the body contacting surface of the device will ultimately contain the agent at the same thermodynamic activity as the reservoir and other elements of device. Thus when such devices are used to administer nicotine, a substantial amount of nicotine can be in the adhesive layer when applied to the skin. These high concentrations of nicotine in the adhesive layer and in direct contact with the skin may cause irritation or sensitization or produce undesirably high nicotine plasma levels during the initial period after application to the skin. In addition to the deleterious effects on the subject which may be caused by high concentrations of nicotine in the adhesive, most adhesives have their physical and adhesive properties degraded by such high concentrations of nicotine.

SUMMARY OF THE INVENTION

According to our invention, we have provided a method for administering nicotine from transdermal patches for approximately 16 hours that is effective in smoking cessation therapy by applying a nicotine patch, capable of administering nicotine at efficacious rates for at least 16 hours, to the skin upon waking and removing it prior to sleep. This method does not administer nicotine during sleep and has been found effective in smoking cessation therapy even though many smokers experience morning craving. It also overcomes the shortcomings associated with oral or buccal nicotine dosage forms, such as the indigestion or jaw soreness associated with nicotine chewing gum.

In a preferred embodiment of our invention, the patch is a device which overcomes problems associated with delivering nicotine transdermally, which include irritation, sensitization and potential over dosage due to high concentrations of nicotine in the in-line adhesive and the adverse effects such concentrations can have on the physical and adhesive properties of the adhesive.

It is accordingly an object of this invention to provide a method for administering nicotine in smoking cessation therapy by applying a nicotine patch upon waking and removing it prior to sleep.

It is another object of this invention to deliver nicotine transdermally for approximately 16 hours a day for smoking cessation therapy by applying to the skin a patch capable of delivering nicotine at an effective rate for at least 16 hours. This patch is applied upon waking and removed prior to sleep and preferably comprises a rate controlled, subsaturated transdermal nicotine delivery device having an in-line adhesive utilizing a subsaturated reservoir, preferably at a nicotine thermodynamic activity no greater than about 0.5, containing an amount of nicotine sufficient to prevent the activity from decreasing by more than about 75% and preferably less than about 25% during the predetermined delivery period.

BRIEF DESCRIPTION OF THE DRAWINGS

The invention will be described in further detail with reference to the accompanying drawings wherein.

DESCRIPTION OF THE INVENTION

Figure 1:
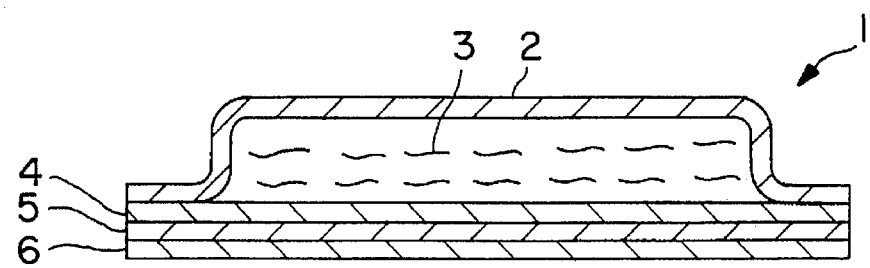
FIG. 1 is a cross-sectional view of an embodiment of transdermal delivery devices usable according to this invention.
Figure 2:
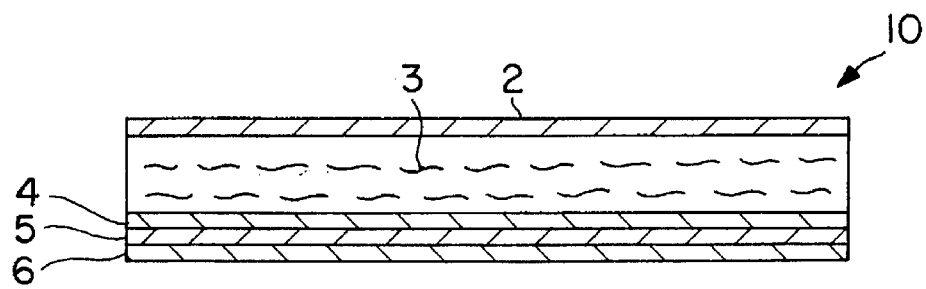
FIG. 2 is a cross-sectional view of the prepared embodiment of the transdermal delivery device usable according to this invention.

Referring now to FIGS. 1 and 2 (like reference numerals referring to common elements), transdermal delivery devices 1 and 10 usable in this invention are shown. Devices 1 and 10 are formed of an impermeable backing 2, a subsaturated nicotine reservoir 3, a nicotine release rate controlling membrane 4, and an in-line contact adhesive 5 permeable to the passage of nicotine. A strippable release liner 6 is also included and is adapted to be removed from the adhesive layer prior to application to the skin of the subject to whom the nicotine is to be administered.

The embodiments of FIGS. 1 and 2 differ in that in FIG. 1 the impermeable backing 2 is heat sealed at its periphery to the rate controlling membrane 4 to form a pouch fully enclosing reservoir 3 to prevent it from flowing or oozing. In the embodiment of FIG. 2 the reservoir 3 has sufficient viscosity to maintain its structural integrity without a peripheral or circumferential seal. In both embodiments, nicotine is present in the reservoir 3 in an amount below the saturation concentration. Arrangements of the adhesive, and reservoir, other than those of FIGS. 1 or 2, are usable according to this invention. For example, an adhesive having microcapsules dispersed therethrough as shown in aforementioned U.S. Pat. No. 3,598,123, which microcapsules could contain nicotine at a thermodynamic activity less than 1. Patches of the type described in U.S. Pat. Nos. 4,758,434 or 4,839,174 could also be used.

The in vitro nicotine release rate or flux, from preferred transdermal delivery devices usable according to this invention, directly into an infinite sink can be considered to consist of two phases, a first, initial "transient" phase, and a second, subsequent "steady-state" delivery phase. During the initial transient phase, the nicotine is released at a high rate as a result of the initial loading of nicotine in the adhesive and rate controlling membrane layers, 5 and 4, respectively. This initial pulse decreases relatively rapidly until the initial loading of nicotine in the adhesive layer is depleted and the "steady-state" phase in which nicotine is being delivered from reservoir 3 through rate controlling membrane 5 commences.

Figure 3:
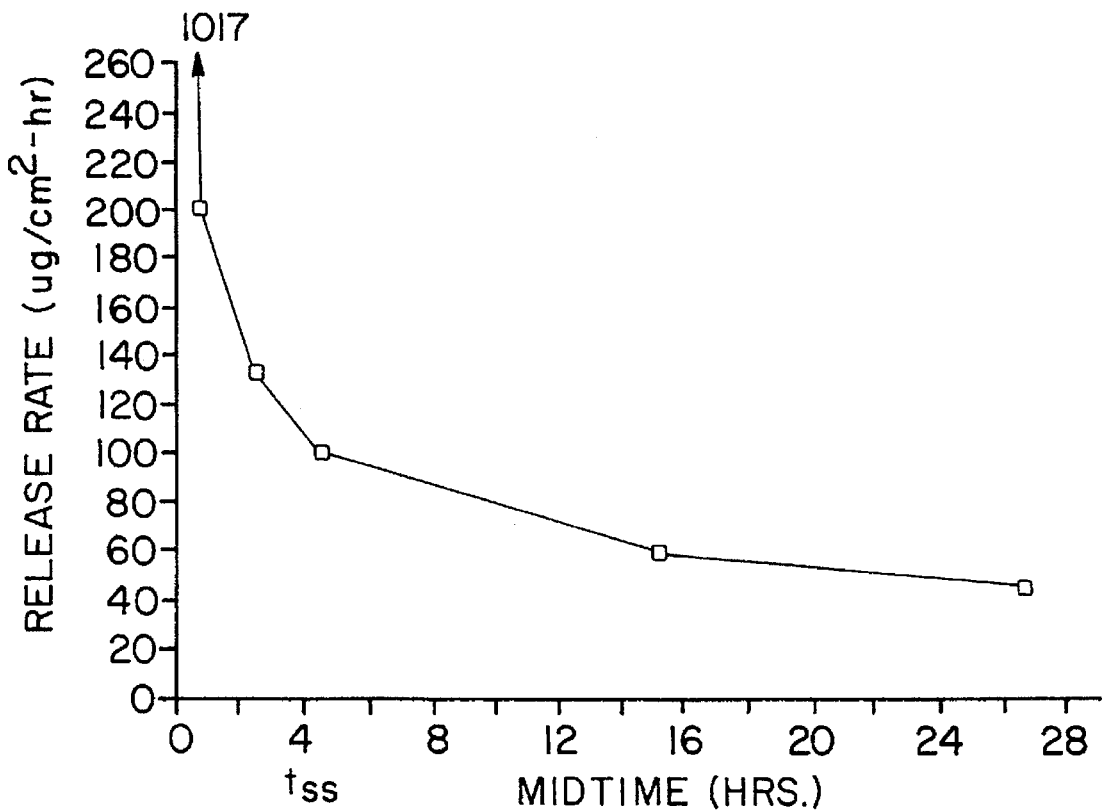
FIG. 3 contains a plot of the in vitro release rates at 35° C. vs. time, for an embodiment of a nicotine patch usable according to this invention.

FIG. 3 illustrates the in vitro release rate of preferred subsaturated nicotine systems usable according to this invention. The data points on the time line represent the midtime between sampling points. Thus, the average release rate is measured between $t_1$ and $t_2$, and is plotted at midtime $t_i$, where $t_i$ is midway between $t_1$ and $t_2$. The $t_{ss}$ position indicated on FIG. 3, represents the approximate time at which the initial transient phase ends and the steady state delivery phase commences.

The steady-state in vitro release rate the preferred devices usable in our invention can be maintained substantially constant from the termination of the initial transient phase until the expiration of the predetermined administration period. As used herein, the in vitro nicotine delivery rate is considered to be "substantially constant" if the steady-state rate does not vary more than about ±50%, and preferably no more than ±25%, during the steady-state administration period.

The maximum allowable concentration of nicotine in the adhesive will be determined by such factors as the nicotine concentration at which the adhesive properties may be impaired, the nicotine concentration at which irritation problems or unacceptably high initial transdermal nicotine fluxes, for example, are observed. When such undesirable effects occur, the initial activity of nicotine in the adhesive should preferably be at a lower level. Because the device will equilibrate upon standing, the activity (but not necessarily the concentration) of nicotine in the reservoir will ultimately be the same as the activity of nicotine in the adhesive layer.

Preferred transdermal devices usable for the delivery of nicotine according to our invention have the following characteristics:

1. The device utilizes an in-line adhesive to maintain the device on the skin;
2. The initial equilibrated concentration of the nicotine in the reservoir 3 and the adhesive 5 is below saturation, expressed alternatively, the thermodynamic activity is less than 1.0 and preferably in the range of about 0.050–0.50; and
3. The initial loading of the nicotine in reservoir 3 is sufficient to prevent the activity of the nicotine in the reservoir from decreasing by more than about 75% and preferably no more than about 25% during the predetermined period of administration.

When the preferred embodiment includes a rate-controlling membrane:

4. The reservoir 3 comprises the nicotine dissolved in a solvent with respect to which the rate controlling means 4 is preferably substantially impermeable; and
5. The thicknesses of the adhesive, rate controlling membrane and reservoir layers are selected so that at least 50% and, preferably at least 75% of the initial equilibrated nicotine loading is in the reservoir layer.

Studies with nicotine releasing gum (Nicorette®), have determined that the target blood level of nicotine for reducing the urge to smoke is approximately 12–15 nanograms/ml and that the clearance of nicotine from the body occurs at about 18 ml/min-kg. An estimate of the target transdermal administration rate can be made from this data.

A 70 kg person, for example, would have a target input rate of:

$$(70 \text{ kg})(18 \text{ ml/min-kg})(60 \text{ min/hr})(0.012 \text{ μg/ml})=907 \text{ μg/hr}$$

For a 20 cm² transdermal system, the average target flux would be:

$$(907 \text{ μg/hr})/(20 \text{ cm}^2)=45 \text{ μg/cm}^2\text{-hr}$$

These calculations are merely illustrative of the invention and are not meant to be limiting in any manner.

To account for individual variability, target steady-state in vivo administration rates within the range of about 250–4000 μg/hr with a typical average rate being about 1000 μg/hr are contemplated. The flux of nicotine through skin varies somewhat from individual to individual and from body site to body site but generally appears to be in the range of about 400–950 μg/cm² hr. Accordingly the preferred administration rates can be readily achieved according to our invention in a rate controlled device having a size in the range of about 5–50 cm². A one day delivery period can readily be obtained from subsaturated devices of this invention, and administration periods of about 8–10 hours and up to about 3 days can be attained by varying the thickness of the reservoir.

Although administration periods of 24 hours have the advantage of application and removal of the device occurring simultaneously at the same time each day, other administration periods, such as about 16 hours, have also proved effective. Such an administration period can be achieved by applying the device each day upon waking, wearing it all day, and removing and discarding the device just prior to sleep. This pattern would be repeated for as long as smoking cessation therapy is desired. In this pattern no nicotine is administered to the subject during the period of sleep. The total nicotine loading in the transdermal delivery devices preferably used in this invention is at least about 50 mg with the equilibrated concentration of nicotine in the reservoir composition being within the range of 5-50 wt %, corresponding to an activity within the range of 0.05-0.50 if the nicotine is miscible with the reservoir composition.

Reaction of the skin to nicotine is flux dependent and to minimize skin reaction it is preferred to maintain the average transdermal flux, particularly with the longer administration periods of about 16 hours or more, below about 200 µg/cm$_2$-hr and preferably to maintain the steady state transdermal flux below about 120 µg/cm2-hr. Typically, the steady-state flux will be in the range of about 30 to 70 µg/cm$^2$-hr.

The equilibrated nicotine loading in the reservoir layer is preferably selected to be sufficient to enable the total dose of nicotine delivered during the 16 hour administration period to be delivered while maintaining the decrease in activity of the nicotine in the reservoir within the limits noted above. The total loading of nicotine in each layer of the device can be readily varied without changing the activity, simply by increasing or decreasing the volume of the adhesive, rate controlling means and/or reservoir means and also by appropriate selection of the total surface area of the device through which nicotine is delivered. Because the rate controlling means can only act as a release rate limiting element on the nicotine which is in the reservoir, the reservoir volume or thickness should be selected with respect to the thicknesses of the rate controlling means and the adhesive, such that at least half, and preferably substantially more, of the initial equilibrated nicotine loading is in the reservoir.

Various materials suited for the fabrication of the various components are disclosed in the aforementioned patents. The matrix of reservoir 3 is preferably anhydrous and suitable materials include, without limitation, natural and synthetic rubbers or other polymeric materials, thickened mineral oils or silicone fluids or petroleum jelly. The preferred embodiment according to this invention is fabricated from an ethylene vinyl acetate (EVA) copolymer of the type described in U.S. Pat. No. 4,144,317, preferably having a vinyl acetate (VA) content within the range of about 28-60 weight percent.

The reservoir may also include dyes, pigments, inert fillers, diluents, antioxidants, antibacterials, stabilizers, vehicles, anesthetics, rubefacients, antipruritics, gelling agents and other conventional components of pharmaceutical products or transdermal therapeutic systems, as are well known in the art.

The rate controlling membrane 5 may be of a dense polymer film that has the requisite permeability to nicotine. The membrane material would be selected such that the flux of the nicotine through the membrane directly into a sink is preferably no greater than the in vitro flux of nicotine across skin (which would produce about 50% system control) and preferably substantially less.

The fractional control of nicotine, $J_{net}/J_{device}$, delivered across skin from the rate controlled transdermal therapeutic system of this invention may be determined from the following relationships where $J_{net}$ is the transdermal nicotine flux from the device, $J_{device}$ is the in vitro release rate of nicotine from the device directly into a sink and $J_{skin}$ is the permeability of the skin to nicotine:

$$J_{net}/J_{device}=[(J_{device}/J_{skin})+1]^{-1}$$

Thus, if the $J_{skin}$, which is typically in the range of 400-950 µg/cm$^2$ hr., is greater than $J_{device}$ by a factor of about 2.4, i.e., $J_{device}$ is in the range of about 170-395, the fractional control of nicotine flux from the system would be:

$$J_{net}/J_{device}=[(1/2.4)+1]^{-1}=0.7$$

Therefore, approximately 70% of the rate control is obtained from the system, and $J_{net}$ would be in the range of about 115-280. Because of the high permeability of skin and the low net flux required, system control in the range of 95-98% can be readily achieved according to this invention.

Preferably the rate controlling membrane 4 is substantially impermeable to the component of reservoir 3 in which the nicotine is dissolved. However, this invention also contemplates use of a rate controlling membrane that is permeable to the passage of components of the reservoir such as anesthetics, rubefacients, permeation enhancers, and antipruritics for example.

Examples of the types of polymer films that may be used to make the membrane 16 are disclosed in U.S. Pat. No. 3,797,494 and 4,031,894, both of which are incorporated herein by reference. Particularly suitable materials are low density polyethylene, high density polyethylene and ethylene vinyl acetate copolymers.

The composition and thickness of adhesive layer 5 is selected such that the adhesive does not constitute a significant permeation barrier to the passage of nicotine and is compatible with nicotine at the activity chosen for the device. Numerous adhesives are known to the art for use as transdermal in-line adhesives. Suitable adhesive materials are listed in the aforementioned patents, a preferred adhesive being a polyisobutylene adhesive of the type described in the aforementioned application of Wang, et al. Amine resistant adhesives, such as silicone adhesives which may be modified with silicone to obtain the desired tack,are also useful in this invention.

The backing member 2 serves the purposes of preventing passage of the drug or environmental moisture through the surface of the reservoir distant from the skin, and also for providing support for the system, where needed. The backing layer is impermeable to the passage of nicotine and can be flexible or nonflexible. Suitable materials include, without limitation, polyethylene terephthalate, some types of nylon, polypropylene, metallized polyester films, polyvinylidene chloride and aluminum foil.

Having thus generally described our invention, the following description and Examples will illustrate and describe various embodiments of our invention.

EXAMPLE I

Subsaturated transdermal nicotine delivery devices were made by extruding a 0.13 mm thick drug reservoir film comprising a subsaturated solution of 40% nicotine base in 60% EVA (40% VA) between an impermeable, pigmented aluminized polymer backing (Medpar™) and a high density polyethylene (HDPE) rate-controlling membrane 0.05 mm thick. This trilaminate was laminated to adhesives consisting of blends of low molecular weight (35K) polyisobutylene (LMW PIB) and high molecular weight (1.2M) polyisobutylene (HMW PIB) in weight ratios of LMW:HMW of (A) 80:20, (B) 85:15 and (C) 90:10, that were solvent cast to a thickness of 0.05 mm from n-heptane solution onto a 0.076 mm strippable release liner formed of fluorocarbon diacrylate/polyethylene terephthalate (PET), (3M 1022) or siliconized PET and allowed to reach equilibrium. All samples exhibited good adhesive properties and had 24 hour average in vitro release rates ($J_{device}$) into water at 37° C. of 60 µg/cm$^2$ hr, 70 µg/cm$^2$ hr, and 72 µg/cm$^2$ hr respectively.

EXAMPLE II

Devices were fabricated according to the procedures of Example I using PIB adhesive blends of LMW:HMW of 75:25 and 80:20 and substituting, as the drug reservoir, a mixture of 70 wt % EVA-40 and 30 wt % nicotine base. The weight percent of the nicotine in the adhesives upon equilibration was found to be about 11 weight percent. Devices were fabricated according to the procedures of Example I, using a PIB adhesive of Formula B, and reservoir compositions of 20%, 30% and 40% nicotine base in EVA-40. The weight percent of nicotine in the PIB adhesive after equilibration was found to be as follows: 8 wt. percent in the 20% nicotine reservoir device; 10 wt. percent in the 30% nicotine reservoir device; and 14 wt. percent in the 40% nicotine reservoir device.

The devices had an initial nicotine loading of 5.2 mg/cm$^2$ for a total loading of 78 mg. After 24 hours the nominal residual nicotine loading was 54 mg corresponding to a decrease in activity of approximately 52%.

EXAMPLE III

Transdermal nicotine delivery devices fabricated as set forth in Example I were cut into fifteen square centimeter devices, using LMW:HMW PIB adhesive blends of 90:10 and 85:15 having a nominal average administration rate of about 1 mg/hr.

These devices were used in clinical studies to evaluate their safety and efficacy as an aid to the withdrawal of smoking in healthy adult cigarette smokers, motivated to stop smoking. The devices were compared to placebos in blind studies for periods of four weeks in a pilot study and six weeks in a definitive study in different treatment regimes involving (a) application upon waking in the morning with removal and reapplication 24 hours later and (b) application upon waking and removal at bedtime, approximately 16 hours thereafter, followed by reapplication in the morning.

Safety was evaluated by noting any reactions that may have occurred during the study and efficacy was evaluated by determining the number and percentage of patients who smoked no cigarettes during the last two weeks of the pilot study and the last four weeks of the definitive study as ascertained by patient questionnaires and corroborated by measurement of expired carbon monoxide at levels of less than or equal to 8 parts per million. Morning craving for cigarettes, incidents of insomnia and severity of withdrawal symptoms were also assessed. A follow-up after approximately 6 months on those patients who smoked no cigarettes during the last two weeks of the study was also made.

Based on the results of these studies it appears that the transdermal nicotine in both 16 and 24 hour regimes was more effective, as compared to the placebo, in both short term and long term smoking cessation and that the incidence of serious skin reaction was low. In a sensitization study using 2.5 cm$^2$ test samples formed from the formulation using the 90:10 adhesive blend described above only 3 out of 186 participants became sensitized.

EXAMPLE IV

Transdermal delivery devices for the controlled delivery of nicotine were prepared utilizing a highly permeable, amine resistant silicone adhesive available from Dow Corning (X7-2920), low density polyethylene (LDPE) as the rate controlling membrane, EVA (40% VA) as the non-diffusible drug reservoir diluent, pigmented medium density polyethylene/aluminized polyester as the impermeable backing member and nicotine base as the source of nicotine. Nicotine is extremely soluble (essentially miscible) in the EVA (40% VA) diluent and thus the weight percent concentration in the diluent corresponds approximately to the thermodynamic activity. The devices tested had 4 mil (0.1 mm) LDPE rate controlling membranes, and 6 mil (0.15 mm) drug reservoirs containing either 20 or 25 weight percent nicotine base. The adhesive layer was cast to a dry thickness of 2 mils (0.05 mm). In vitro skin flux data for these devices are shown in Table I. The nicotine flux data across skin was obtained from averaging the data generated by systems tested on two different skin donors.

TABLE I

| Time (hr) | Drug Flux with 20 wt % drug (µg/cm2-hr) | Drug Flux with 25 wt % drug (µg/cm2-hr) |
| --- | --- | --- |
| 2 | 87.9 | 133.2 |
| 4 | 65.8$t_{ss}$ | 104.6$t_{ss}$ |
| 6 | 52.6 | 85.0 |
| 8 | 47.5 | 73.2 |
| 23.25 | 33.4 | 52.8 |
| 27.25 | 27.9 | 45.2 |
| 30.75 | 23.1 | 40.3 |

Thicker rate controlling and adhesive layers would provide a higher initial pulse as compared to thinner layers which would provide a smaller initial pulse for the same initial activity. $T_{ss}$ indicates the approximate time of commencement of the steady state.

EXAMPLE V

Nicotine transdermal delivery devices 1 cm$^2$ were fabricated comprising a 30 wt % nicotine/70 wt % EVA 40 reservoir composition (0.30 nicotine activity), a 2 mil (0.05 mm) high density polyethylene (HDPE) rate controlling membrane and a 2 mil (0.05) amine resistant silicone adhesive layer (Dow Corning X7-2920 with 5 wt % silicone fluid). The in vitro release rate at 35° C. is shown in FIG. 3. A system at least 10 cm$^2$ in size, designed according to the embodiment of Example II and having a 50 mg or 5 mg/cm$^2$ drug loading, should deliver nicotine at an average 24 hour administration rate of about 1000 µg/hr. when applied to human subjects on a daily basis.

EXAMPLE VI

Subsaturated systems were fabricated comprising a nicotine/EVA 40 reservoir, a 4 mil (0.10 mm) LDPE rate controlling membrane and an amine resistant in-line adhesive. Systems having varying nicotine activities up to 0.40 were tested on rabbits and guinea pigs and systems having activities of up to 0.40 were tested on humans. These systems were only minimally irritating. We believe that high flux rates associated with systems having high (greater than 0.50) or unit activity may cause irritation. This is evidenced by the fact that of the systems tested on humans, irritation, while still minimal, appeared to increase with increasing activity.

Having thus generally described our invention and preferred embodiments thereof, it is apparent that various modifications and substitutions will be apparent to workers skilled in the art. These modifications and substitutions can be made without departing from the scope of our invention which is limited only by the following claims.

We claim:

1. A method for administering nicotine to an individual in need of such administration comprising:
   a) applying to the skin of said individual upon waking, a transdermal device comprising a nicotine reservoir containing a sufficient quantity of nicotine to maintain a useful transdermal flux of nicotine from said device for a total time period of at least 16 hours;
   b) maintaining said device in nicotine transmitting relationship to the skin during waking hours;
   c) removing said device prior to sleep.

2. The method of claim 1, wherein the time elapsed between application and removal and said device is about 16 hours.

3. The method of claim 1, wherein nicotine is administered to said patient at an administration rate of about 250–4,000 μg/h during a substantial portion of the administration period.

4. The method of claim 3 wherein the average flux of nicotine over the administration period does not exceed 200 μg/cm$^2$/hr.

5. The method of claim 4 wherein the average flux of nicotine over the administration period does not exceed 120 μg/cm$^2$/hr.

6. The method of claim 3 wherein the administration rate is maintained substantially constant over a substantial portion of said administration period.

7. The method of claim 1 wherein the transdermal device comprises a subsaturated nicotine reservoir having a thermodynamic activity of nicotine less than 1.0 and an initial equilibrated loading sufficient to prevent the activity of the nicotine in the reservoir from decreasing by more than 75% over the 16 hour administration period.

8. The method of claim 7 wherein the initial activity is no greater than 0.5.

9. The method of claim 8 wherein the initial nicotine loading is sufficient to prevent the activity from decreasing by more than 25% during the 16 hour administration period.

* * * * *